(12) United States Patent
Cottrell et al.

(10) Patent No.: US 11,445,995 B2
(45) Date of Patent: Sep. 20, 2022

(54) GRADIENT INDEX SCINTILLATOR FOR IMPROVED RESOLUTION

(71) Applicant: Raytheon Company, Waltham, MA (US)

(72) Inventors: William J. Cottrell, Melrose, MA (US); Matthew R. Taylor, Burr Ridge, IL (US)

(73) Assignee: RAYTHEON COMPANY, Waltham, MA (US)

( * ) Notice: Subject to any disclaimer, the term of this patent is extended or adjusted under 35 U.S.C. 154(b) by 0 days.

(21) Appl. No.: 16/913,659

(22) Filed: Jun. 26, 2020

(65) Prior Publication Data

US 2021/0405225 A1 Dec. 30, 2021

(51) Int. Cl.
*A61B 6/03* (2006.01)
*A61B 6/00* (2006.01)

(52) U.S. Cl.
CPC ............ *A61B 6/5258* (2013.01); *A61B 6/037* (2013.01)

(58) Field of Classification Search
CPC .............................. A61B 6/037; A61B 6/5258
See application file for complete search history.

(56) References Cited

U.S. PATENT DOCUMENTS

| | | | |
|---|---|---|---|
| 4,647,779 A | 3/1987 | Wong | |
| 4,677,299 A | 6/1987 | Wong | |
| 6,946,658 B2 | 9/2005 | Tai | |
| 7,087,905 B2 | 8/2006 | Murayama et al. | |
| 7,129,497 B2 | 10/2006 | Wollenweber et al. | |
| 7,679,049 B2 | 3/2010 | Rietzel | |
| 7,683,330 B2 | 3/2010 | Krieg et al. | |
| 8,143,583 B2 | 3/2012 | Gagnon | |
| 8,405,035 B1* | 3/2013 | Nagarkar | G01T 1/2008 250/367 |
| 8,618,489 B2 | 12/2013 | Ohashi et al. | |
| 8,763,430 B2 | 7/2014 | Ichinose et al. | |
| 2011/0042575 A1 | 2/2011 | Ishii et al. | |
| 2014/0192420 A1 | 7/2014 | Baer et al. | |
| 2016/0252628 A1 | 9/2016 | Tonami et al. | |

\* cited by examiner

*Primary Examiner* — David P Porta
*Assistant Examiner* — Shun Lee
(74) *Attorney, Agent, or Firm* — Cantor Colburn LLP

(57) ABSTRACT

A Positron Emission Tomography (PET) device, detector for a PET device and method of performing PET. The detector includes a scintillator and a photodetector. The scintillator includes a crystal defining a receiving axis and having a receiving face for receiving a gamma ray. A dopant concentration of the crystal varies along the receiving axis with a distance from the receiving face. The photodetector is configured to generate an impulse response in response to an interaction between the gamma ray and the crystal. A decay profile of the impulse response is related to a local dopant concentration of the crystal at the location of the interaction and the distance of the interaction from the receiving face.

13 Claims, 6 Drawing Sheets

GRADIENT INDEX SCINTILLATOR FOR IMPROVED RESOLUTION

BACKGROUND

The present disclosure relates to Positron Emission Tomography and specifically to a detector suitable for use in PET and its method of use.

Positron Emission Tomography (PET) has application in various fields including medical imaging. PET involves placing an object within a chamber and recording gamma rays associated with positron emission from the object in order to obtain a three-dimensional image of the object. The chamber is generally a cylindrical shell that has detectors along an inner surface of the shell for measuring an energy of gamma rays associated with positron emission and determining a location of their sources within the object. The resolution of the resulting image is highest for gamma rays that originate at or near the center of the cylindrical shell, since such gamma rays are generally incident at a detector perpendicular to its receiving face and therefore only interact with the same detector crystal regardless of penetration depth. However, the resolution of the image decreases as the distance of the source of the gamma rays from the center increases, since such off-axis gamma rays may interact with different detector crystals, depending on penetration depth. Therefore, there is a need to be able to improve resolution of an image for gamma rays originating from locations away from the center.

SUMMARY

According to one embodiment of the present disclosure, a method of performing Positron Emission Tomography (PET) is disclosed. A gamma ray is received from an object at a scintillator of a detector of the PET, the scintillator including a crystal, the crystal defining a receiving axis and having a receiving face, wherein a dopant concentration of the crystal changes along the receiving axis with distance from the receiving face. An impulse response is generated at a photodetector in response to an interaction between the gamma ray and the crystal, wherein a decay profile of the impulse response is related to the dopant concentration at the distance at which the interaction occurs from the receiving face. The distance of the interaction from the receiving face is determined at a processor based on the decay profile of the impulse response. The object is imaged using the distance of the interaction from the receiving face.

According to another embodiment of the present disclosure, a detector for a Positron Emission Tomography device is disclosed. The detector includes a scintillator and a photodetector. The scintillator includes a crystal defining a receiving axis and having a receiving face for receiving a gamma ray, wherein a dopant concentration of the crystal varies along the receiving axis with a distance from the receiving face. The photodetector is configured to generate an impulse response in response to an interaction between the gamma ray and the crystal, wherein a decay profile of the impulse response is related to a local dopant concentration and the distance of the interaction from the receiving face.

According to yet another embodiment of the present disclosure, a Positron Emission Tomography (PET) device is disclosed. The PET detector includes a detector. The detector includes a scintillator and a photodetector. The scintillator including a crystal defining a receiving axis and having a receiving face for receiving a gamma ray, wherein a dopant concentration of the crystal varies along the receiving axis with a distance from the receiving face. The photodetector is configured to generate an impulse response in response to an interaction between the gamma ray and the crystal, wherein a decay profile of the impulse response is related to a local dopant concentration and the location of the interaction from the receiving face.

Additional features and advantages are realized through the techniques of the present disclosure. Other embodiments and aspects of the disclosure are described in detail herein and are considered a part of the claimed disclosure. For a better understanding of the disclosure with the advantages and the features, refer to the description and to the drawings.

BRIEF DESCRIPTION OF THE SEVERAL VIEWS OF THE DRAWINGS

The subject matter which is regarded as the disclosure is particularly pointed out and distinctly claimed in the claims at the conclusion of the specification. The forgoing and other features, and advantages of the disclosure are apparent from the following detailed description taken in conjunction with the accompanying drawings in which:

DETAILED DESCRIPTION

The present invention provides a detector for use in a Positron Emission Tomography (PET) device. The detector includes a scintillator crystal that interacts with a gamma ray incident on the crystal. The crystal is doped with a dopant material such that the dopant concentration along a selected axis of the crystal displays a gradient. The gradient can take any selected form and concentration level. An impulse response that is created by the detector has a decay profile or decay rate that is a result of the local dopant concentration at the location at which the gamma ray interacts with the crystal. Therefore, a location of the interaction with the crystal can be determined, allowing for greater PET resolution especially for off-axis gamma rays, as discussed below.

Figure 1:
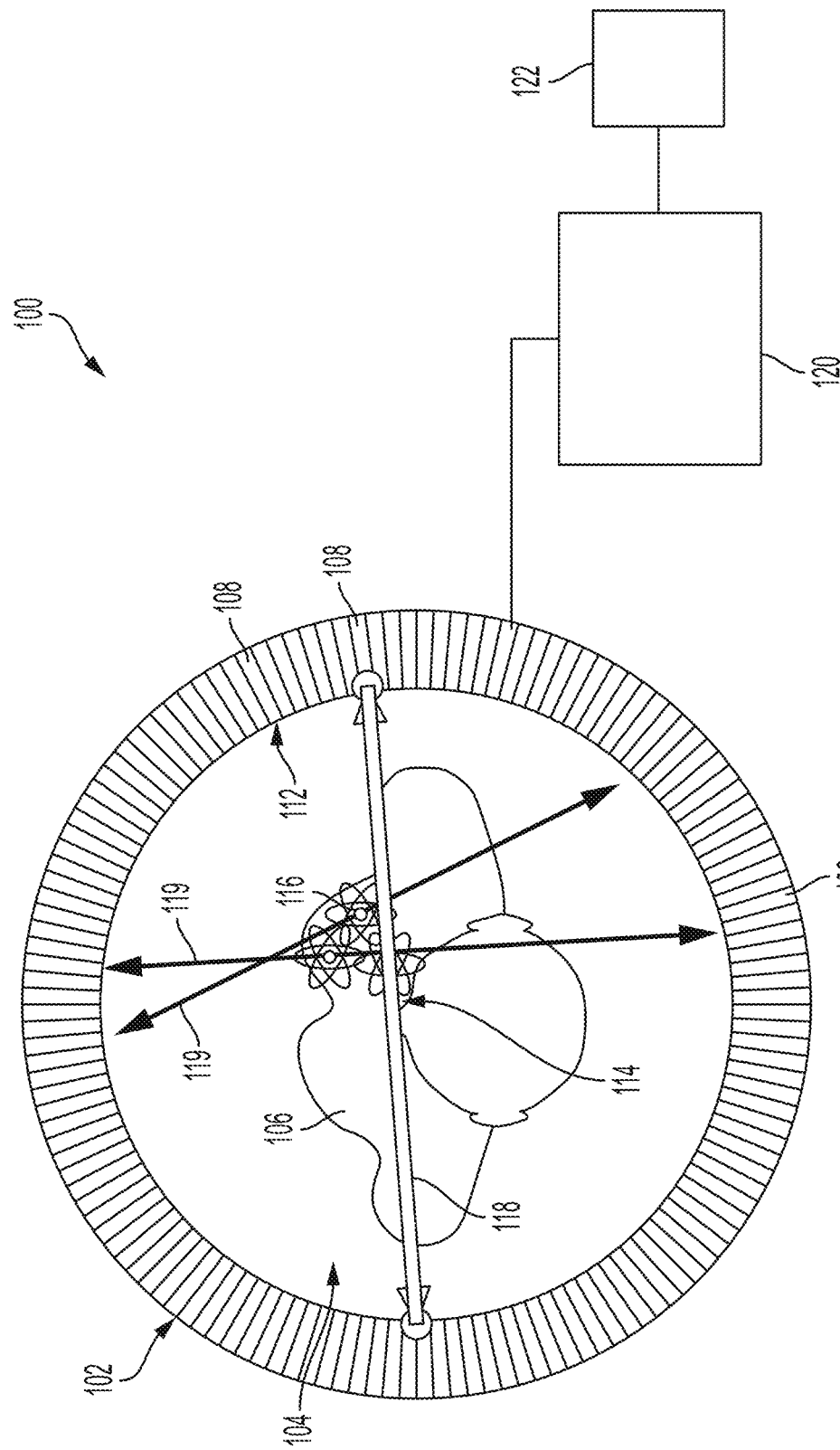
FIG. 1 shows a cross-section of an illustrative Positron Emission Tomography (PET) device, in an embodiment.

FIG. 1 shows a cross-section of an illustrative Positron Emission Tomography (PET) device 100, in an embodiment. The PET device 100 includes a cylindrical shell 102 defining a hollow chamber 104 into which an object 106 can be placed for investigation. The cylindrical shell 102 defines a central axis 114 and includes detectors 108 disposed along its inner surface. Each detector has a receiving face 112 and a receiving axis perpendicular to the receiving face. The receiving axis of a detector 108 is aligned to pass through the central axis 114 of the cylindrical shell 102.

In order for the object 106 to be detected and imaged, radioactive elements 116 are embedded therein, generally prior to placing the object 106 in the chamber 104. The radioactive elements 116 emit positrons which combine with neighboring electrons to produce a pair of gamma rays. Each gamma ray is emitted in the opposite direction from its associated pair (at 180 degrees to each other). Detectors 108 detect these gamma rays and send an electrical signal to a processor 120 in response to the detection. A processor 120 runs a computer program to determine the energy of the gamma rays and thereby determine the location of their corresponding radioactive elements 116 from the electrical signal. The processor 120 further constructs a three-dimensional (3D) image of the object 106 based on the electrical signals. The 3D image can be displayed at a monitor 122.

As shown in FIG. 1, the radioactive elements 116 can be located at or near the central axis 114 of the PET device 100 or substantially away from the central axis 114. A radioactive element 116 located at or near the central axis 114 can generate on-axis gamma rays 118 that enter a detector 108 along a line perpendicular or substantially perpendicular to a receiving face of the detector 108, thereby allowing for a high-resolution image. Highly off-axis radioactive elements 116 however generate off-axis gamma rays 119 that enter a detector 108 at a non-zero angle from the perpendicular line. This non-zero angle can cause resolution errors, as discussed below with respect to FIG. 3.

Figure 2:
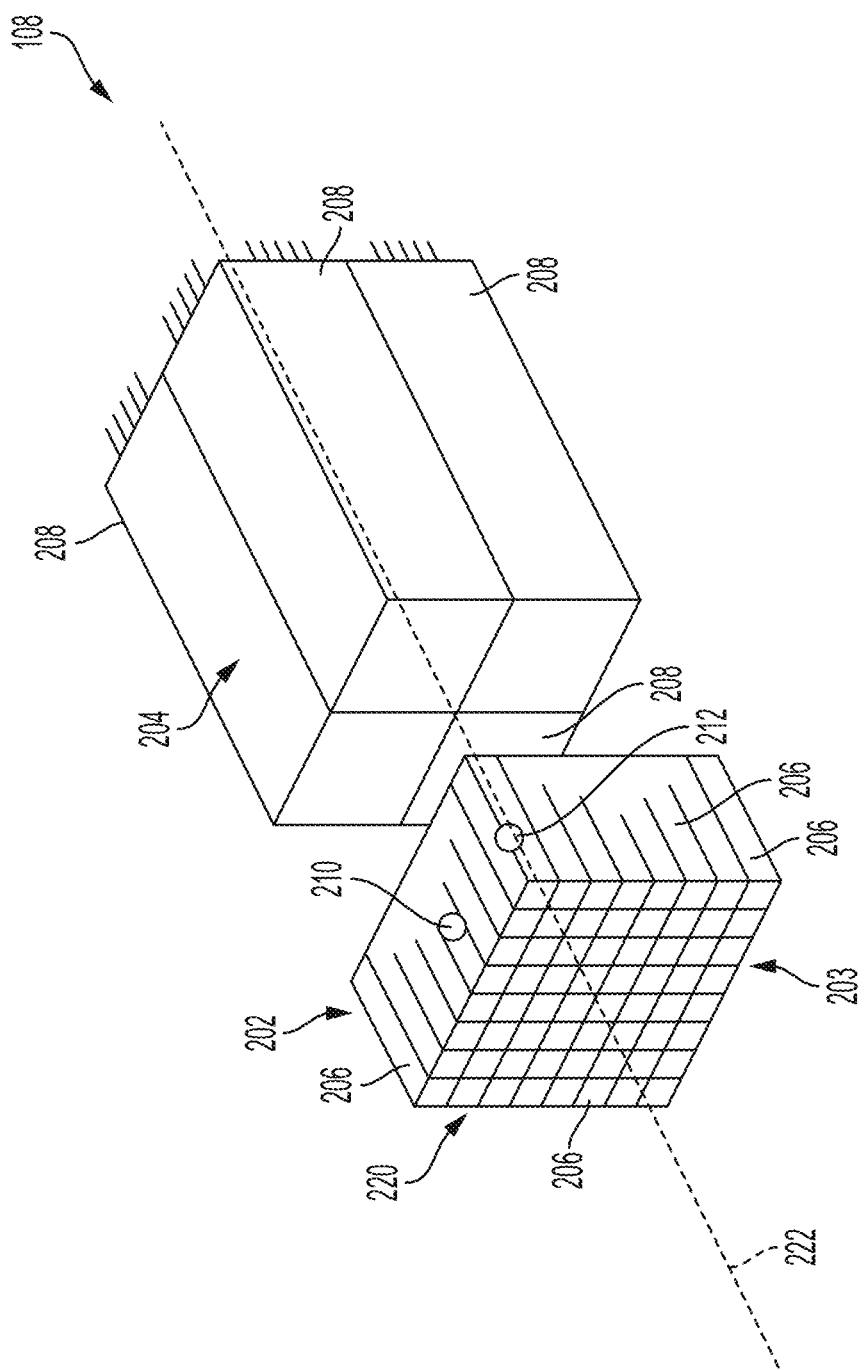
FIG. 2 shows a perspective view of a detector of the PET device of FIG. 1 in an illustrative embodiment.

Referring now to FIG. 2, a perspective view of a detector 108 of the PET device 100 is shown in an illustrative embodiment. The detector 108 includes a scintillator 202 and a photodetector 204. The scintillator 202 can include a single crystal but generally includes a crystal array 203 that includes a plurality of crystals. Various exemplary array sizes include a 6×6 array of 4×8×30 mm$^3$ (length×width×depth) crystals, a 6×6 array of 6.25×6.25×30 mm$^3$ crystals, an 8×8 array of 6.75×6.75×20 mm$^3$ crystals, and an 8×8 array of 4.5×4.8×30 mm$^3$ crystals, among others. A crystal of the crystal array 203 generates a photon when a gamma ray interacts with it. In various embodiments, a crystal of the crystal array 203 can be made of a Bismuth germanate ($Bi_4Ge_3O_{12}$ or BGO) material Lutetium oxyorthosilicate (Lu2(SiO4)O or LSO), Lutetium-yttrium oxyorthosilicate ($Lu_{2(1-x)}Y_{2x}SiO_5$ or LYSO), or Gadolinium Orthosilicate ($Gd_2SiO_5$(Ce) or GSO) among others.

The crystal array 203 has a receiving face 220. A receiving axis 222 is defined that extends perpendicular to the receiving face 220. The receiving axis 222 is a central axis to both the scintillator 202 and the photodetector 204. Each of the plurality of crystals includes a receiving face and an axis that extends parallel to the receiving axis 222. The photodetector 204 can be a photomultiplier tube (PMT) responsive to the photon generated at the scintillator 202. The PMT receives the photon and generates an impulse response in the form of an electrical signal. The electrical signal can be a measurement of voltage or current generated at the PMT. The magnitude of the electrical signal is indicative of an intensity of the photon which is related to an energy of the gamma ray.

In the illustrative embodiment of FIG. 2, each crystal of the crystal array 203 forms a scintillator channel 206. Similarly, the photodetector 204 can be composed of a plurality of photodetector channels 208. Each photodetector channel 208 is assigned to a subset of the scintillator channels 206 and can receive photons from the assigned subset. Using a plurality of scintillator channels 206 and a plurality of photodetector channels 208 improves a spatial resolution of the detector 108. Thus, a first gamma ray interaction occurring at a first location 210 of the scintillator 202 can be differentiated from a second gamma ray interaction at a second location 212 of the scintillator 202.

Figure 3:
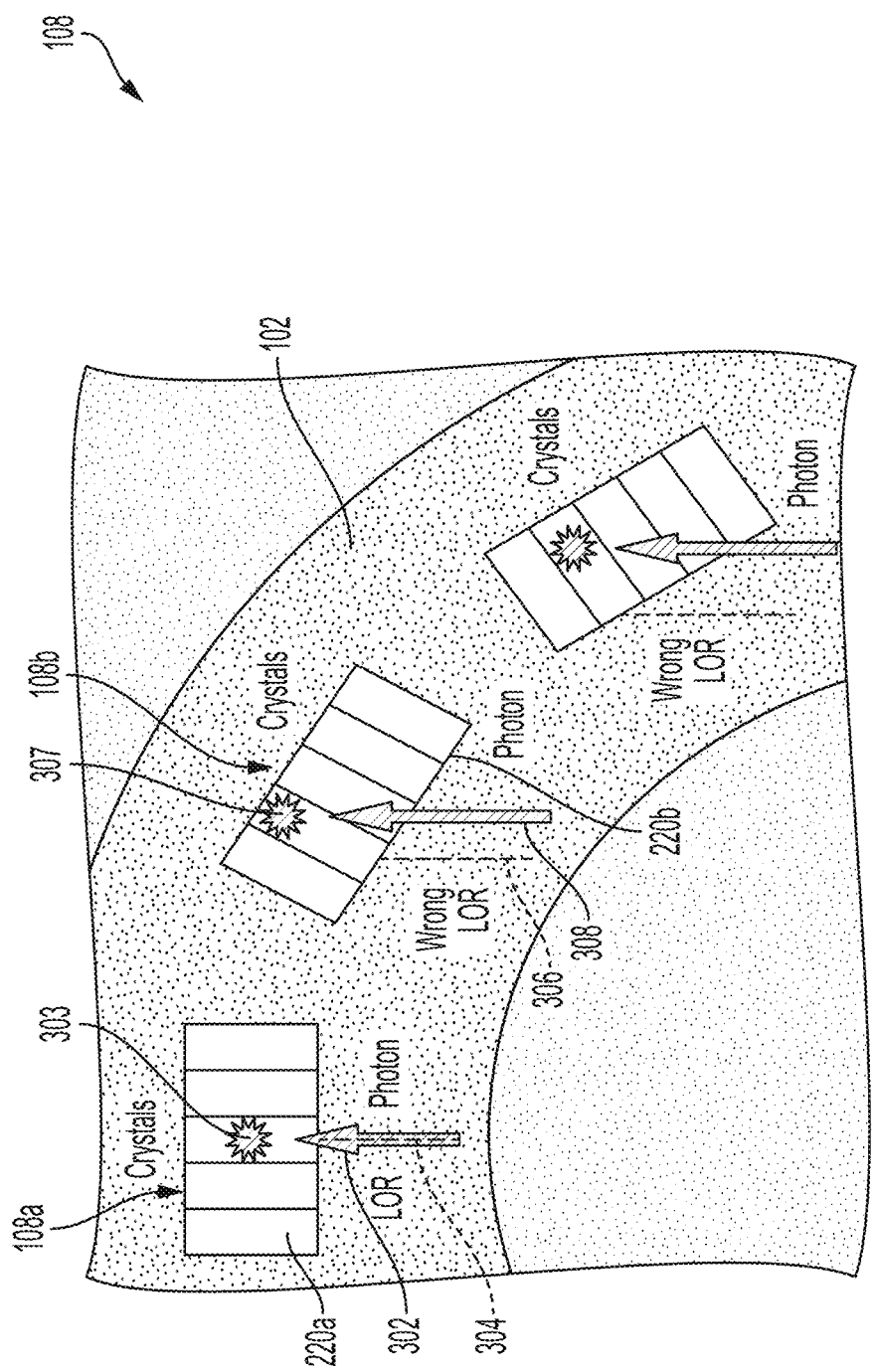
FIG. 3 shows a section of a cylindrical shell of the PET device.

FIG. 3 shows a section of the cylindrical shell 102 of the PET device 100, illustrating resolution problems that can occur in PET for off-axis gamma rays. Detector 108a receives a gamma ray generated from a radioactive element that is at or near the central axis 114 of the cylindrical shell 102. The gamma ray enters the detector 108a along a first line of propagation 302 that is perpendicular or substantially perpendicular to the receiving face 220a of the detector 108a. The interaction 303 between the gamma ray and detector 108a occurs within a single channel of the detector regardless of depth of interaction. The processor 120 constructs a first line of response (LOR) 304 that passes through the interaction 303 and is perpendicular to the receiving face 220a. The first LOR 304 substantially traces the same path as the first line of propagation 302. Thus, the location of the radioactive element that produces the gamma ray is well determined. When a particle impinges on the receiving face 220a as in detector 108a, regardless of penetration depth, the interaction occurs in that same scintillator channel it originally enters.

Detector 108b however is shown receiving a gamma ray from a location that is substantially away from the central axis 114 (off-axis). The gamma ray therefore is incident on the receiving face 220b of the detector 108b at a non-perpendicular angle, as shown by second line of propagation 306. Due to the angle of incidence, the interaction 307 between gamma ray and detector 108b can occur within one of several detector channels of detector 108b depending on depth of interaction. The second LOR 308, which is constructed from receiving face 220b, is generally offset from the first LOR 304, leading to an error in the location of the radioactive element producing the gamma ray and thus leading to resolution errors. For a cylindrical shell having a radius of 60 centimeters, a resolution loss of 1.3 millimeters can be expected for off-axis radioactive elements. For a cylindrical shell having a radius of 100 centimeters, a resolution loss of 2.2 millimeters can be expected for off-axis radioactive elements.

Resolution issues therefore occur due to an ambiguity in the detector crystal when the gamma ray traverses multiple scintillator channels, as illustrated in detector 108b. When the gamma ray is emitted at a location away from the central axis 114, it can traverse multiple scintillator channels and/or photodetector channels, essentially blurring the photodetector's response to the interaction. Resolution issues can be corrected by determining the depth within the scintillator channel at which the interaction occurs. The method disclosed herein determines depth by making a characteristic of the response to the interaction indicative of the depth at which the interaction occurs.

Figure 4:
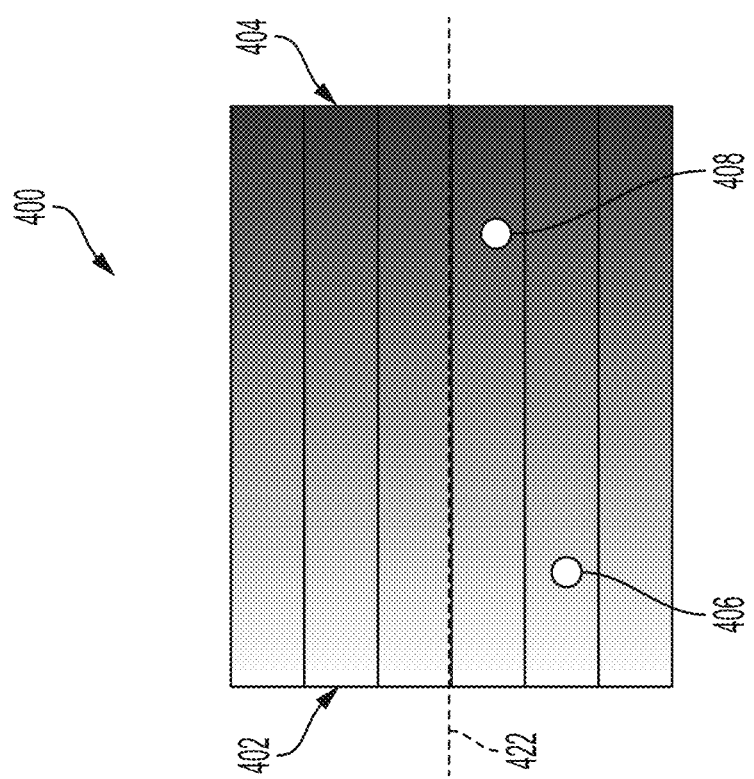
FIG. 4 shows a side view of an illustrative crystal array along a receiving axis of the scintillator suitable for improving a detection resolution for off-center gamma rays.

FIG. 4 shows a side view of an illustrative crystal array 400 along a receiving axis 422 of the scintillator 202 suitable for improving a detection resolution for off-center gamma rays, in an embodiment. The crystal array 400 extends from a receiving face 402 to a back face 404 along the receiving axis 422. The photodetector 204, although not shown in FIG. 4, is placed against the back face 404. The crystal array 400 has a volumetric dopant concentration that changes along a direction of the receiving axis 422. Common dopants include thallium, cerium, sodium-iodide, etc. In one embodiment, the dopant concentration has a lowest dopant concentration at the receiving face 402 and has a highest dopant concentration at the back face 404. In an alternate embodiment, the dopant concentration can be highest at the receiving face 402 and lowest at the back face 404. The variation of the dopant concentration from the receiving face 402 to the back face 404 defines a concentration gradient. For the crystal array 400 of FIG. 4, a plurality of crystals is shown. However, each crystal has the same concentration gradient as its neighboring or adjacent crystal.

Figure 5:
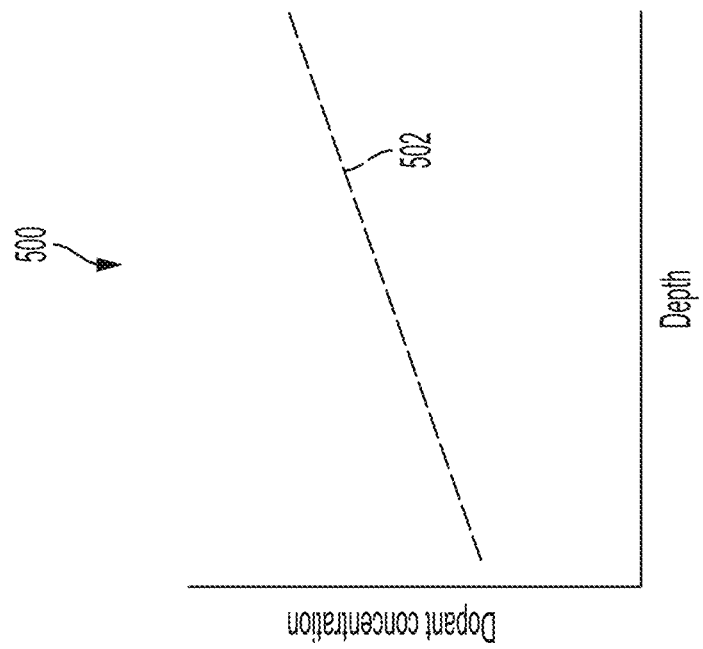
FIG. 5 shows a graph of dopant concentration for the crystal array of FIG. 4.

FIG. 5 shows a graph 500 of dopant concentration for the crystal array 400 of FIG. 4. Distance or depth along the receiving axis 422 is shown along the abscissa with depth=0 corresponding to the location of the receiving face 402. Volumetric dopant concentration is shown along the ordinate axis. The dopant concentration curve 502 shown in the graph 500 exhibits a linear gradient with length. In various embodiments, the gradient can be a linear gradient, a continuous gradient, a stepped gradient or a non-linear gradient (such a quadratic, cubic, etc.) or some combination thereof.

The impulse response associated with a gamma ray-crystal interaction has a characteristic decay rate. For an undoped BGO crystal material, the decay rate is about 300 nanoseconds (ns). For an undoped LSO crystal material the decay rate is about 40 ns and for an undoped GSO crystal material, the decay rate is about 60 ns. For a doped crystal material (either, BSO, LSO, GSO), a decay rate of an impulse response associated with a gamma ray-crystal interaction is dependent on the local volumetric dopant concentration at the location within the crystal array. Thus, a decay rate of an impulse response associated with a first interaction 406 occurring at a first distance from the receiving face 402 is different than a decay rate of an impulse response associated second interaction 408 occurring at a second distance from the receiving face 402. The decay rate of the impulse response can be measured to determine a distance between the location of its corresponding gamma ray-crystal interaction and the receiving face 402. Alternatively, the location can be determined with respect to the back face 404 or equivalently from the photodetector 204. Given a better understanding of the location of the interaction within the crystal array, a LOR can be drawn that better represents the path of the gamma ray that produced the interaction, thereby allowing for greater spatial resolution, especially for off-axis gamma rays.

Figure 6:
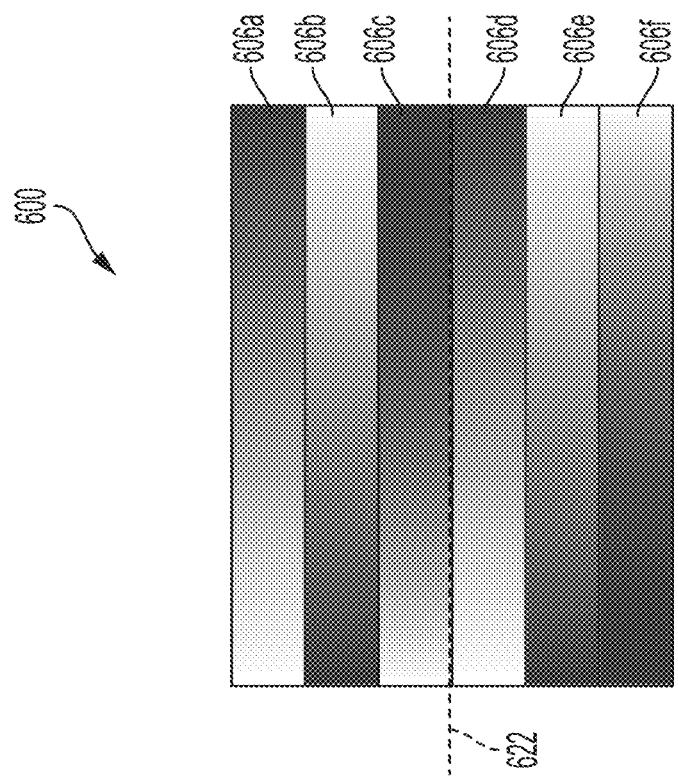
FIG. 6 shows a side view of a crystal array along a receiving axis, in another embodiment.

FIG. 6 shows a side view of a crystal array 600 along a receiving axis 622, in another embodiment. The crystal array 600 includes a plurality of crystals 602a-602f, each crystal defining a scintillator channel. Each crystal has an assigned or individual dopant concentration and/or dopant concentration gradient. In general, the dopant concentration gradient for a selected crystal is different from the dopant concentration gradient for an adjacent or neighboring crystal.

In an embodiment, the crystal array includes a first crystal (e.g., 602a) defining a first scintillator channel and a second crystal (e.g., 602b) defining a second scintillator channel. The first crystal has a first dopant concentration having a first gradient along the receiving axis, and the second crystal has a second dopant concentration having a second gradient along the receiving axis, whereas the second gradient is different from the first gradient. The processor can therefore identify in which of the first scintillator channel and the second scintillator channel an interaction occurs. The processor can then determine a distance between the interaction and the receiving face from the decay profile of the corresponding impulse response and the gradient of the identified channel, which is known to the processor.

Figure 7:
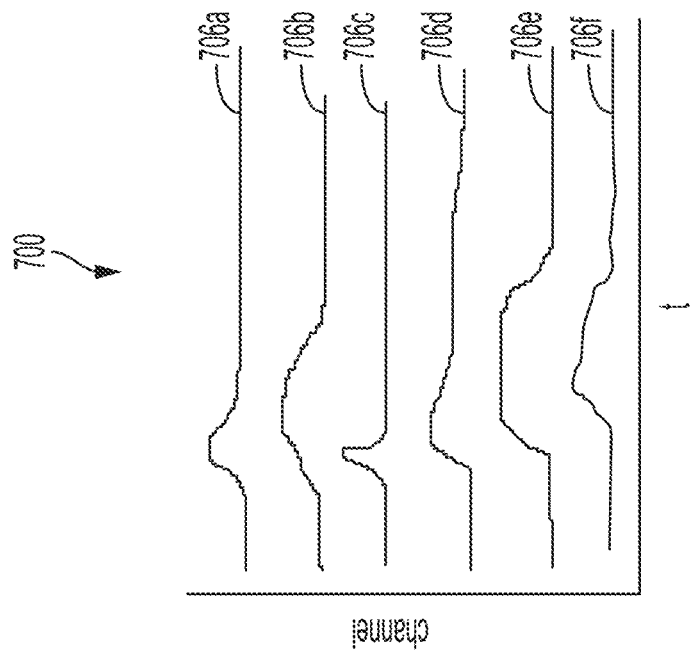
FIG. 7 shows a graph of impulse responses for each of the plurality of crystals of FIG. 6.

FIG. 7 shows a graph 700 of impulse responses for each of the plurality of crystals 602a-602f of FIG. 6. Time is shown along the abscissa and channels are represented along the ordinate axis. Impulse responses 702a-702f are associated with crystals 602a-602f, respectively. Each of the impulse responses 702a-702f has a separate or individual decay rate or decay profile. The decay rate or decay profile of a selected impulse response is based on the local dopant concentration at the location of the associated gamma-ray crystal interaction, which is indicative of the distance of the interaction from the receiving face (or back face). The photodetector 204 and processor 120 can therefore identify a crystal or scintillator channel in which an interaction occurs from the presence of the impulse response and then determine the distance of the interaction from the receiving face of the identified scintillation channel from the decay rate or decay profile of the impulse response, as well as knowledge of the dopant concentration gradient of the identified scintillator channel. Improved determination of the location of the gamma ray-crystal interaction, improves the determination of the corresponding radioactive element and improved resolution, especially for off-axis gamma rays.

Figure 8:
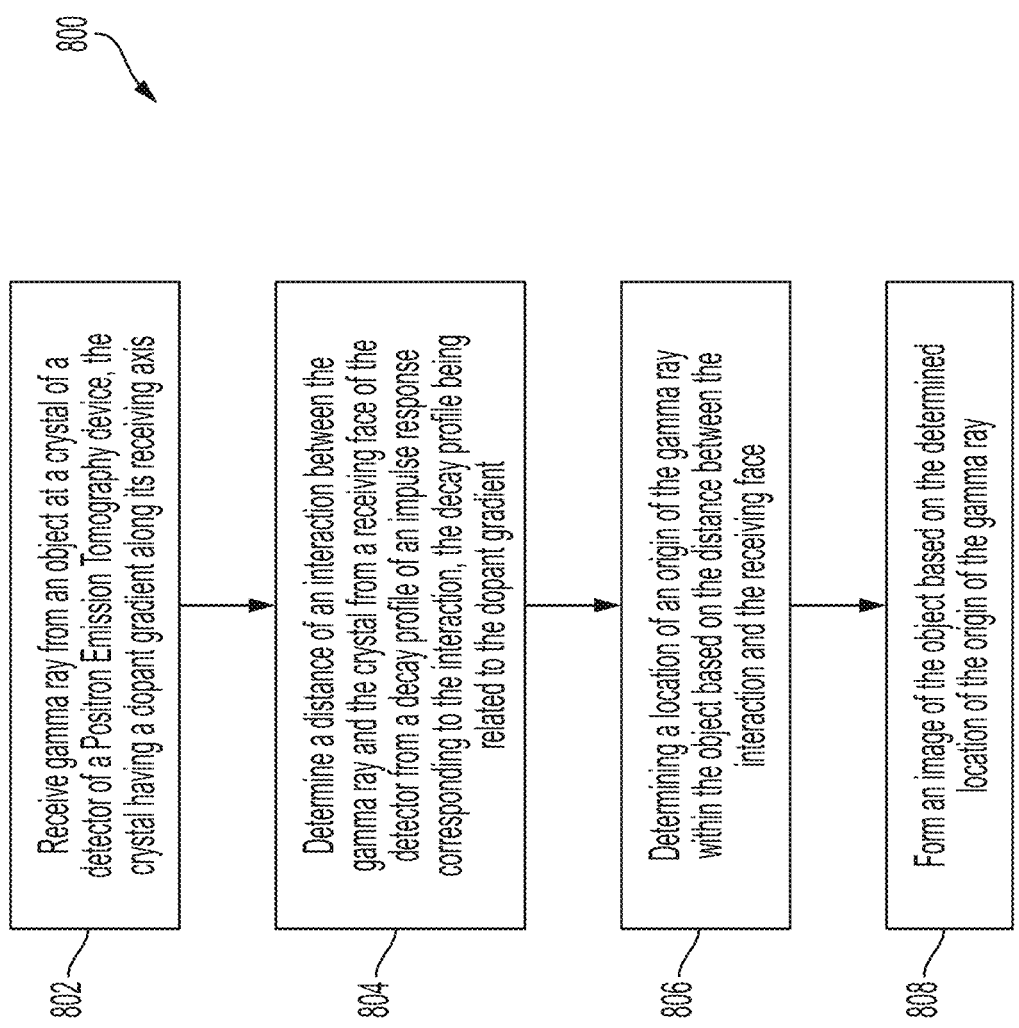
FIG. 8 shows a flowchart for forming an image of an object using the PET device disclosed herein.

FIG. 8 shows a flowchart 800 for forming an image of an object using the PET device disclosed herein. In box 802, a gamma ray is received from the object at a crystal of a detector of the PET device. The crystal having a dopant gradient along its receiving axis, as described herein. In box 804, a distance of an interaction between the gamma ray and the crystal from a receiving face of the detector is determined from a decay profile of an impulse response corresponding to the interaction, the decay profile being related to a dopant gradient at a location of the interaction. In box 806, a location of an origin of the gamma ray within the object is determined based on the determined distance between the interaction and the receiving face. In box 808, an image of the object is formed based on the determined location of the origin of the gamma ray.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for exemplary embodiments with various modifications as are suited to the particular use contemplated.

While the exemplary embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method of performing Positron Emission Tomography (PET), comprising:
    receiving a gamma ray from an object at a scintillator of a detector of the PET, the scintillator including a first crystal defining a first scintillator channel and a second crystal defining a second scintillator channel, each of the first crystal and the second crystal extending from a receiving face of the detector along a receiving axis perpendicular to the receiving face, wherein the first crystal has a first dopant concentration having a first gradient along the receiving axis and the second crystal has a second dopant concentration along the receiving axis, the second gradient being different than the first gradient and at least one of the first gradient and the second gradient is quadratic or higher;
    generating an impulse response at a photodetector in response to an interaction between the gamma ray and one of the first crystal and the second crystal, wherein a decay profile of the impulse response is related to the dopant concentration at the distance at which the interaction occurs from the receiving face;
    determining, at a processor, the distance of the interaction from the receiving face based on the decay profile of the impulse response and the one of the first scintillator channels and the second in which the interaction occurs; and
    imaging the object using the distance of the interaction from the receiving face.

2. The method of claim 1, wherein the decay profile includes a decay rate of the impulse response.

3. The method of claim 1, further comprising determining, at a processor, the distance of the interaction from the receiving face based on the decay profile of the impulse response and the local dopant concentration at the distance.

4. The method of claim 1, further comprising receiving at one of the first crystal and the second crystal at a non-zero angle to the receiving axis.

5. A detector for a Positron Emission Tomography device, the detector comprising:
    a scintillator including a first crystal defining a first scintillator channel and a second crystal defining a second scintillator channel, each of the first crystal and the second crystal extending from a receiving face along a receiving axis perpendicular to the receiving face, wherein the first crystal has a first dopant concentration having a first gradient along the receiving axis and the second crystal has a second dopant concentration along the receiving axis, the second gradient being different than the first gradient and at least one of the first gradient and the second gradient is quadratic or higher; and
    a photodetector configured to generate an impulse response in response to an interaction between the gamma ray and one of the first crystal and the second crystal, wherein a decay profile of the impulse response is related to a local dopant concentration of the at least one of the first crystal and the second crystal in which the interaction occurs and the distance of the interaction from the receiving face.

6. The detector of claim 5, further comprising a processor configured to determine the selected distance of the interaction from the receiving face based on the decay profile of the related impulse response and the local dopant concentration.

7. The detector of claim 5, wherein the decay profile is related to a local dopant concentration at the selected distance from the receiving face.

8. The detector of claim 5, wherein the decay profile includes decay rate of the impulse response.

9. The detector of claim 5, further comprising a processor configured to identify in which of the first scintillator channel and the second scintillator channel the interaction occurs from the presence of the impulse response and determining a distance of the interaction from the receiving face from the decay profile of the impulse response and the gradient of the identified channel.

10. A Positron Emission Tomography (PET) device, comprising:
    a detector comprising:
        a first scintillator including a first crystal, the first crystal extending along a receiving axis and having a receiving face perpendicular to the receiving axis for receiving a gamma ray, wherein a first dopant concentration of the first crystal having a first gradient along the receiving axis with a distance from the receiving face; and
        a second scintillator including a second crystal extending along the receiving axis and having a receiving face perpendicular to the receiving axis for receiving a gamma ray, wherein a second dopant concentration of the second crystal having a second gradient along the receiving axis with a distance from the receiving face, wherein the second gradient is different from the first gradient and at least one of the first gradient and the second gradient is quadratic or higher; and
        a photodetector configured to generate an impulse response in response to an interaction between the gamma ray and one of the first crystal and the second crystal, wherein a decay profile of the impulse response is related to a local dopant concentration and the location of the at least one of the first crystal and the second crystal in which the interaction occurs and the distance of the interaction from the receiving face.

11. The PET device of claim 10, further comprising a processor configured to determine the selected distance of the interaction from the receiving face based on the decay profile of the related impulse response and the local dopant concentration.

12. The PET device of claim 10, wherein the decay profile includes decay rate of the impulse response.

13. The PET device of claim 10, further comprising a processor configured to identify in which of the first scintillator channel and the second scintillator channel the interaction occurs from the presence of the impulse response and determining a distance of the interaction from the receiving face from the decay profile of the impulse response and the gradient of the identified channel.

* * * * *